United States Patent [19]

Tsuda

[11] Patent Number: 5,842,980
[45] Date of Patent: Dec. 1, 1998

[54] MAGNETIC RESONANCE INSPECTING METHOD AND APPARATUS

[75] Inventor: Munetaka Tsuda, Mito, Japan

[73] Assignee: Hitachi Medical Corporation, Tokyo, Japan

[21] Appl. No.: 870,593

[22] Filed: Jun. 6, 1997

Related U.S. Application Data

[63] Continuation of Ser. No. 361,296, Dec. 22, 1994, abandoned.

[30] Foreign Application Priority Data

Dec. 28, 1993 [JP] Japan ................................. 5-337112

[51] Int. Cl.$^6$ .................................................. A61B 5/055
[52] U.S. Cl. ........................................... 600/410; 600/413
[58] Field of Search ................................. 600/407, 410, 600/411, 413; 324/307, 309, 318, 322

[56] References Cited

U.S. PATENT DOCUMENTS

| | | | |
|---|---|---|---|
| 4,736,751 | 4/1988 | Gevins et al. | 128/732 |
| 4,901,141 | 2/1990 | Costello | 324/318 |
| 4,940,057 | 7/1990 | Kamei | 128/653.2 |
| 5,076,275 | 12/1991 | Bechor et al. | 128/653.2 |
| 5,325,854 | 7/1994 | Ehnholm | 128/653.2 |
| 5,339,813 | 8/1994 | DeYoe et al. | 128/653.5 |
| 5,352,979 | 10/1994 | Conturo | 324/307 |
| 5,438,989 | 8/1995 | Hochman et al. | 128/653.1 |

Primary Examiner—Brian Casler
Attorney, Agent, or Firm—Antonelli, Terry, Stout & Kraus, LLP

[57] ABSTRACT

A person to be inspected lies on his back on the tabletop of the patient table. The person is moved together with the tabletop so that the head of the person which is the inspection part, coincides with almost the center of the superconductive magnet. A control circuit controls the operations of a power source for a gradient magnetic field and a radio frequency transmission and reception circuit. The control circuit furthermore outputs a control signal to a light emitter control circuit, which controls a light emitter, which emits light in a predetermined color into a magnet space so as to change the quantity of light and color tone in the magnet space. Light emission and the magnetic resonance inspection sequence are synchronized with each other. An type of irritation may be given to the person to be inspected, such a by sound, heat, or electric signal, in place of light.

33 Claims, 12 Drawing Sheets

MAGNETIC RESONANCE INSPECTING METHOD AND APPARATUS

This application is a continuation application of Ser. No. 08/361,296, filed Dec. 22, 1994 now abandoned.

BACKGROUND OF THE INVENTION

The present invention relates to an inspecting method and apparatus for magnetic resonance inspection and, more particularly, to an inspecting method and apparatus for magnetic resonance inspection which is suited to measuring values of the density distribution and relaxation time of a specific atomic nucleus (for example, hydrogen atomic nucleus, phosphorus atomic nucleus, etc.) of the tissue of a living body non-invasively using a magnetic resonance phenomenon and to obtaining images and spectrum information for medical diagnosis.

Conventionally, a nuclear magnetic resonance (hereinafter referred to as just NMR) phenomenon is used to study the molecular structure of an organic compound. A typical NMR apparatus for analysis used for this object is designed so as to handle a comparatively small sample of a substance to be studied. However, an imaging technique to be used to extract anatomical information of a living body using an NMR phenomenon in the same way as with an X-ray CT apparatus and ultrasonic diagnostic apparatus has been developed recently. It has been made clear that an image for expressing a parameter, such as the relaxation time of nuclear spin (mainly hydrogen atomic nucleus), has the value in a medical diagnosis to judge the condition of health of tissue in the inspection area. In addition to the hydrogen atomic nucleus, by generating an NMR spectrum of, for example, an atomic nucleus, such as a phosphorus atom at a specific position of a living body, an attempt to obtain information concerning the metabolic function of tissue has been studied.

The NMR phenomenon is generated in relation to an atomic nucleus having an odd number of protons or neutrons constituting the tissue of the human body. Each atomic nucleus has a magnetic moment due to the spin of protons or neutrons. When the human body consisting of such atomic nucleuses, is arranged in a uniform static magnetic field Bo, many nuclear magnetic moments generate a magnetization M in the direction of the magnetic field. The nuclear magnetic moments execute a precession around the axis of the magnetic field at a frequency depending on the intensity of the applied magnetic field Bo. The angular frequency of this precession omega is called a Larmor frequency and is expressed by $\omega=\gamma Bo$ ($\gamma$ indicates a constant which is called a gyromagnetic ratio). When a radio frequency magnetic field which coincides with the Larmor frequency omega is applied in this state, the atomic nucleuses execute a resonance absorption. When the application of this radio frequency magnetic field is stopped, the atomic nucleuses return to the thermal equilibrium state with a time constant determined by the relaxation time. This behavior of the atomic nucleuses, that is, changes in the magnetization M generate an electromotive force in the coils arranged in the neighborhood by electromagnetic induction. This electric signal is detected. However, the imaging apparatus requires a device for discriminating the position of the human body from which the signal is derived. Therefore, in the magnetic resonance imaging apparatus, a gradient magnetic field whose intensity varies with the position of the body in the three axial directions X, Y, and Z, which intersect each other orthogonally, is overlaid on the static magnetic field so as to encode spatial information into an NMR signal. This NMR signal is processed by a computer so as to obtain target inspection data.

Generally in the case of the pulse sequence shown in FIG. 2 which will be explained later as an example, the repetitive time of the pulse sequence (the time from application of the first radio frequency pulse in the pulse sequence to application of the first radio frequency pulse in the next pulse sequence) is set to about 0.1 to 2 seconds and the number n of NMR signals to be obtained is set to 128 to 256. An image of an m by n matrix size (m indicates the number of sampling points of each NMR signal) in this case is obtained within about 30 seconds to 10 minutes.

It has been many years since the magnetic resonance inspecting apparatus started to be used clinically in 1982, though the inspecting method and apparatus have been improved continuously since that time at an active pace. Firstly, it can be pointed that the intensity of the static magnetic field has been increased from 0.04 tesla to 1.5 tesla. Since the intensity of an NMR signal increases as the intensity of the static magnetic field increases, the increase in the intensity of static magnetic field is extremely effective in improving the signal-to-noise ratio of the inspection data. Next, an improvement in the pulse responsiveness in the gradient magnetic field and a improvement in the performance of the radio frequency coils can be pointed out. These improvements and the improvement in the signal-to-noise ratio has enabled a remarkable reduction in the inspection time. For example, when the repetitive time of the pulse sequence shown in FIG. 2 is set to 4.9 ms, an image of a 64 by 128 matrix size can be obtained within 350 ms.

Furthermore, an experiment for observing the status of the tissue of the human body in real time using an imaging method, which is called an echo planer imaging method (EPI) as shown in FIG. 6, which will be explained later has been started. According to this experiment, the time required for measuring an image is generally within the range from 10 ms to 50 ms though it depends on the matrix size. Since this shortened inspection time is quite short compared with that of the physiological motion of the human body, a new possibility for medical diagnosis is made available in the magnetic resonance inspecting method in which medical diagnosis has heretofore been impossible by using the conventional imaging method, which requires several minutes to ten or more minutes. In other words, the magnetic resonance inspecting method not only provides anatomical information, but also can observe various functions of the human body. For example, the motion of the heart can be diagnosed in real time and a change in the susceptibility due to the inflow effect of blood into the brain tissue accompanying the perceptual action each time can be observed. Particularly, when the object of the inspection is to measure the active status of the brain tissue of a person to be inspected quantitatively, it is necessary to reflect a difference in the susceptibility or spin—spin relaxation time $T_2$ due to the blood amount flowing into the brain tissue before and after activating the brain tissue to obtain a difference in the image density.

Such a magnetic resonance inspecting method is described in "Innervisions of functional MRI", INNERVISION (7·8) 1992, pp. 43–50.

However, there is no relation between the means for activating the brain tissue and the imaging means in the conventional magnetic resonance inspecting method and apparatus. As a result, it is difficult to specify whether the inspection data is caused by activation or for another reason.

Therefore, it is desired to improve the reliability of the inspection data.

SUMMARY OF THE INVENTION

An object of the present invention is to provide an improved magnetic resonance inspecting method and apparatus having a brain tissue activation means which is suitable for obtaining function imaging or spectra of the brain tissue of the human body.

The magnetic resonance inspecting method relating to the present invention is an inspecting method using nuclear magnetic resonance which, from one viewpoint, generates a static magnetic field in a predetermined space including an inspection object, generates each of a gradient magnetic field and a radio frequency magnetic field with a space in the predetermined timing and intensity, detects a nuclear magnetic resonance signal from the inspection object, conducts processing for the detected signal, and displays the operation result, wherein the method gives an irritation to the sense organ of the inspection object in practical connection with the operation timing of each of the gradient magnetic field and the radio frequency magnetic field and detects the nuclear magnetic resonance signal from the inspection object immediately afterward.

The magnetic resonance inspecting apparatus relating to the present invention has, from one viewpoint, a magnetic field generating means for generating a static magnetic field, a gradient magnetic field and a radio frequency magnetic field in a predetermined space including an inspection object, a means for giving an irritation to the sense organ of the inspection object in practical connection with the magnetic field generation timing for generating each of the gradient magnetic field and the radio frequency magnetic field, a signal detection means which is installed in the predetermined space and detects a nuclear magnetic resonance signal from the inspection object, an electronic computer for inputting the detected nuclear magnetic resonance signal, performing a predetermined operation for the nuclear magnetic resonance signal according to the computer program which is stored in the electronic computer beforehand, and outputting the operation result, and a display means for displaying the operation result using the electronic computer.

The inspecting apparatus relating to the present invention has, from another viewpoint, a magnetic field generating means for generating a static magnetic field, a gradient magnetic field and a radio frequency magnetic field in a predetermined space including an inspection object, a means for activating the brain tissue of the inspection object, a signal detection means which is installed in the predetermined space and detects a nuclear magnetic resonance signal from the inspection object, an electronic computer for inputting the detected nuclear magnetic resonance signal, performing a predetermined operation for the nuclear magnetic resonance signal according to a computer program which is stored in the electronic computer beforehand, and outputting the operation result, a control means which is connected between the magnetic field generation means, the brain tissue activation means, and the electronic computer to effect control so that the activation of the brain tissue is executed in practical connection with the magnetic field generation timing for generating each of the gradient magnetic field and the radio frequency magnetic field, and a display means for displaying the operation result using the electronic computer.

From still another viewpoint, the aforementioned inspecting apparatus has a structure such that the aforementioned means for giving an irritation to the sense organ is a physical irritation giving means and any irritations other than the physical irritation by the physical irritation giving means will not be inputted substantially into the corresponding sense organ of the aforementioned inspection object. This structure has a structure for physically shielding at least one part of the inspection object. Where the physical irritation is a contact pressure, for example, which will be described later, this shielding means is not necessary.

From a further viewpoint, in the aforementioned magnetic resonance inspecting apparatus, an irritation given from the aforementioned means for giving an irritation to the sense organ may be light from a light emitter, sound from a sounding body, heat from a heating unit, a current or voltage from an electrode, contact pressure such as by hand, a smell from a smell emitter, or a taste from a taste producer.

Objects and characteristics of the present invention other than the above will be made clear by explanation of the following embodiments which will be executed with reference to the accompanying drawings.

DESCRIPTION OF THE PREFERRED EMBODIMENTS

Figure 1:
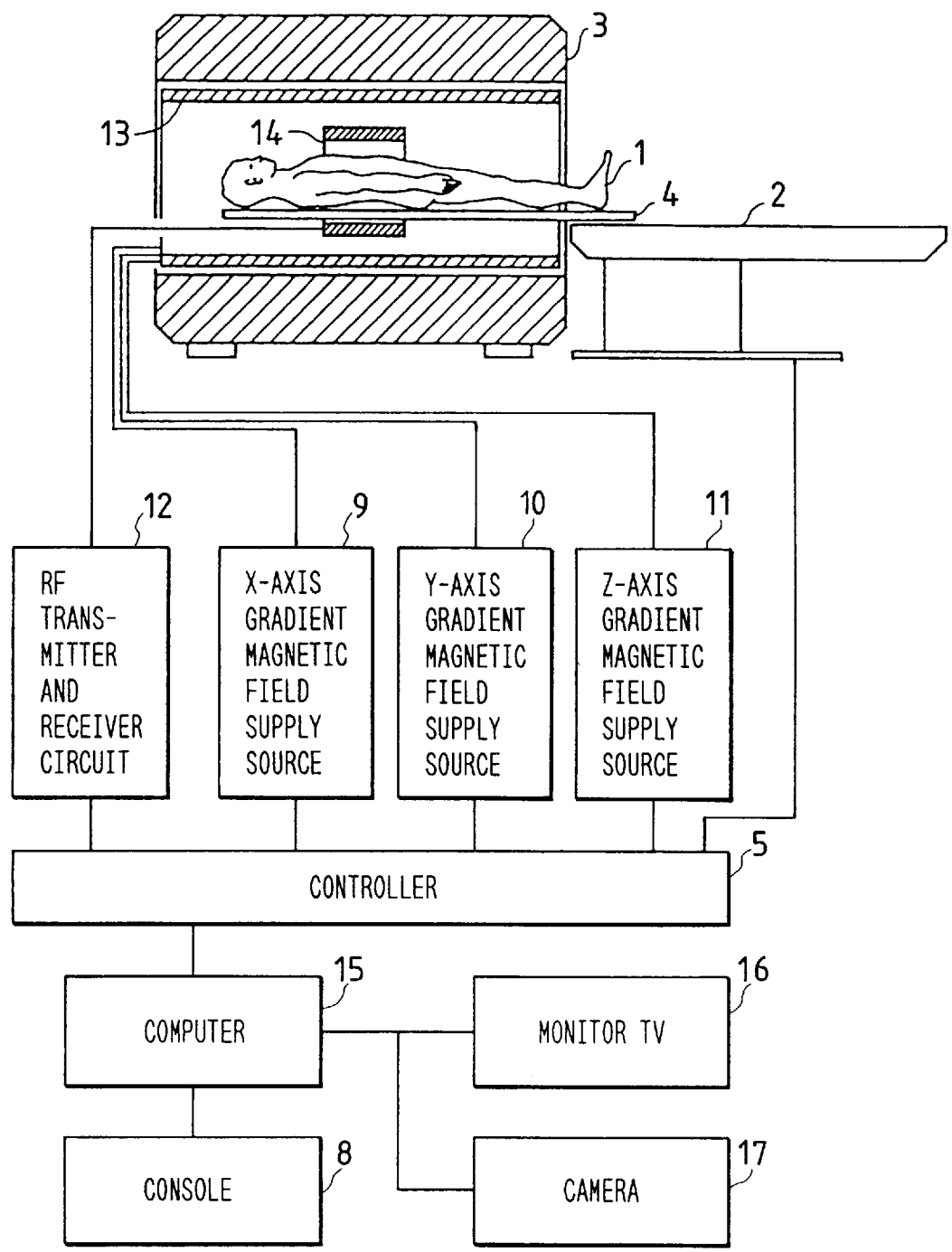
FIG. 1 is a block diagram of a magnetic resonance inspecting apparatus showing a conventional embodiment.

To assist to understand the present invention, before starting an explanation of the embodiments of the present invention, the conventional apparatus will be explained briefly with reference to FIG. 1. The magnetic resonance inspecting apparatus shown in FIG. 1 consists of a superconductive magnet 3 (there are a permanent magnet and an ordinary conductive electric magnet type available) for generating a uniform static magnetic field, a gradient magnetic field coil 13 for generating a gradient magnetic field for giving position information to a nuclear magnetic resonance signal at the inspection part of a person to be inspected 1 who lies on his back on a tabletop 4, gradient magnetic field power sources 9, 10, and 11 for supplying a driving current to the field coil 13, a radio frequency coil 14 for generating a radio frequency magnetic field for exciting a nuclear spin at the inspection part and for detecting the precession of the nuclear spin as an electric signal, a radio frequency transmission and reception circuit 12 for driving the coil 14, an electronic computer 15 for executing signal processing for converting an NMR signal to an image, a monitor display 16 for displaying an image after signal processing, a camera 17 for imaging, a control circuit 5 for controlling each unit with a predetermined timing, a patient table 2 for moving the person to be inspected 1, and an operator console 8.

Figure 2:
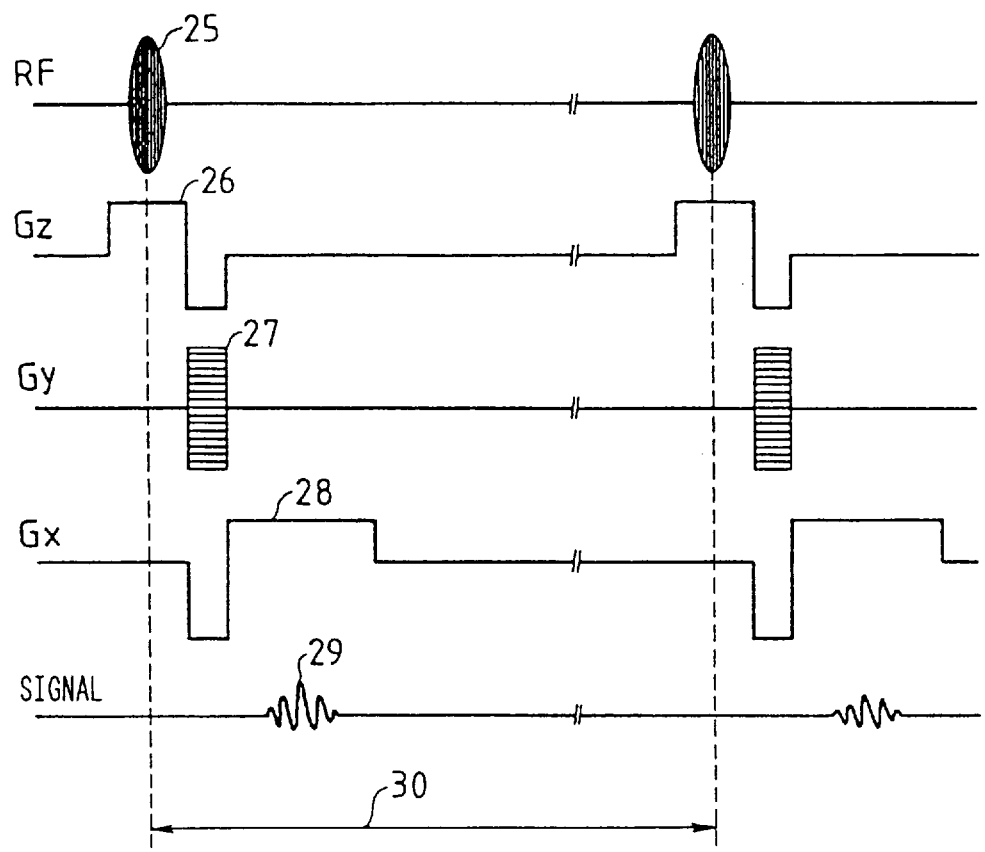
FIG. 2 is a pulse diagram representing an example of a pulse sequence which is used together with the apparatus shown in FIG. 1.

A case in which this apparatus is used to pick up a cross sectional image of the abdomen of the human body will be explained according to the pulse sequence shown in FIG. 2. When a pulse 26 of a gradient magnetic field Gz is given in the z axial direction and a pulse 25 of the resonance excitation radio frequency magnetic field RF having a narrow-band frequency spectrum is irradiated at the same time, only the nuclear spin existing in a specific narrow area delta z in the z axial direction is selectively excited. When an NMR signal S is detected by executing frequency modulation by a pulse 28 of a gradient magnetic field Gx in the x axial direction, the coordinate value in the x axial direction proportionally corresponds to the NMR signal (sampled at m points) which is detected at that point. The coordinate value in the y axial direction proportionally corresponds to the phase of the NMR signal which is detected at the point (this is referred to as phase encoding and it is accomplished by adding a pulse 27 of a gradient magnetic field Gy in the y axial direction to the excited nuclear spin for a fixed period of time). Furthermore, the NMR signal is measured n times by proportionally changing the coefficient thereof and the frequency of the NMR signal when this measuring count n is taken as a time variable corresponds to the coordinate value in the y axial direction.

Figure 3:
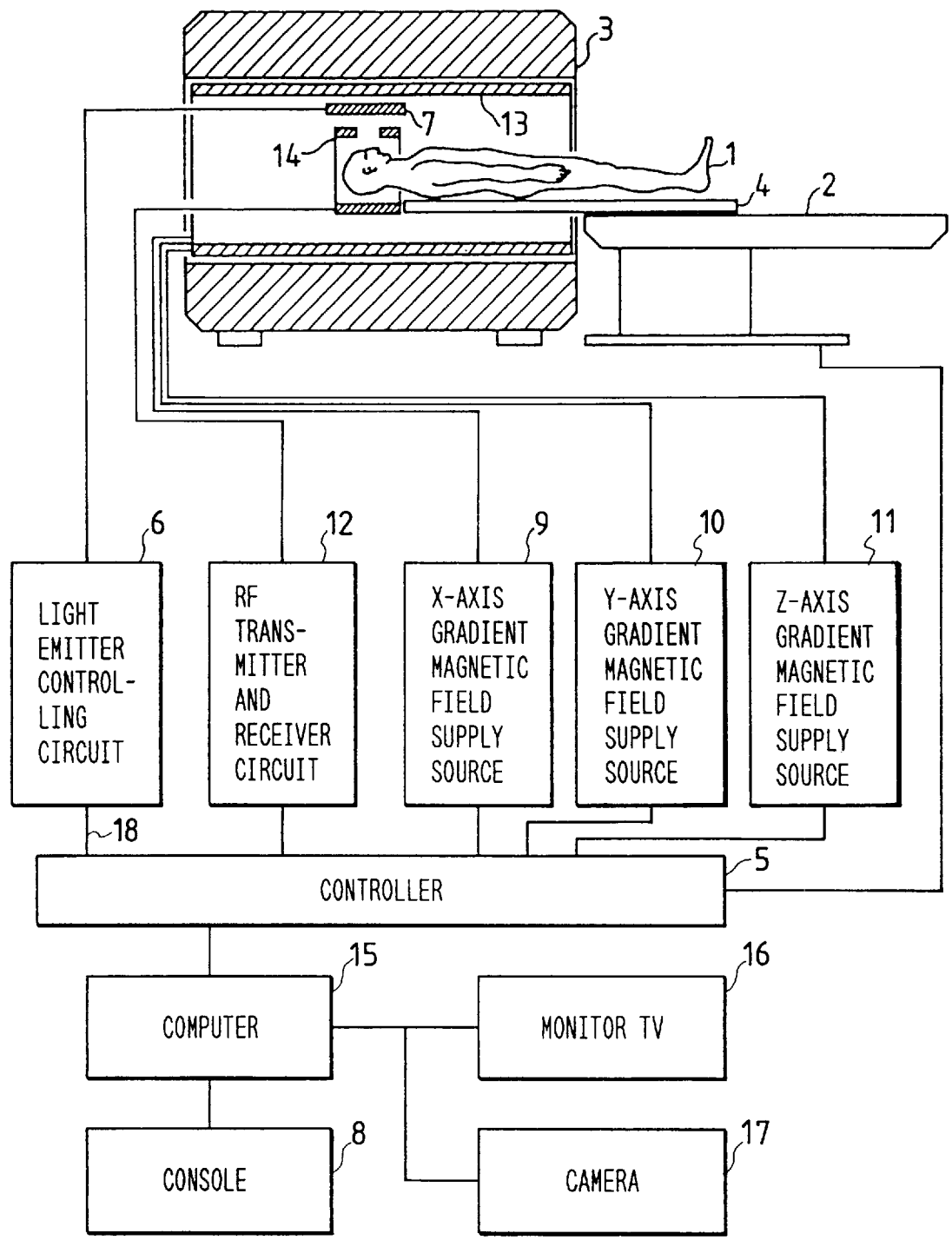
FIG. 3 is a block diagram of a first embodiment of the magnetic resonance inspecting apparatus based on the present invention.
Figure 4:
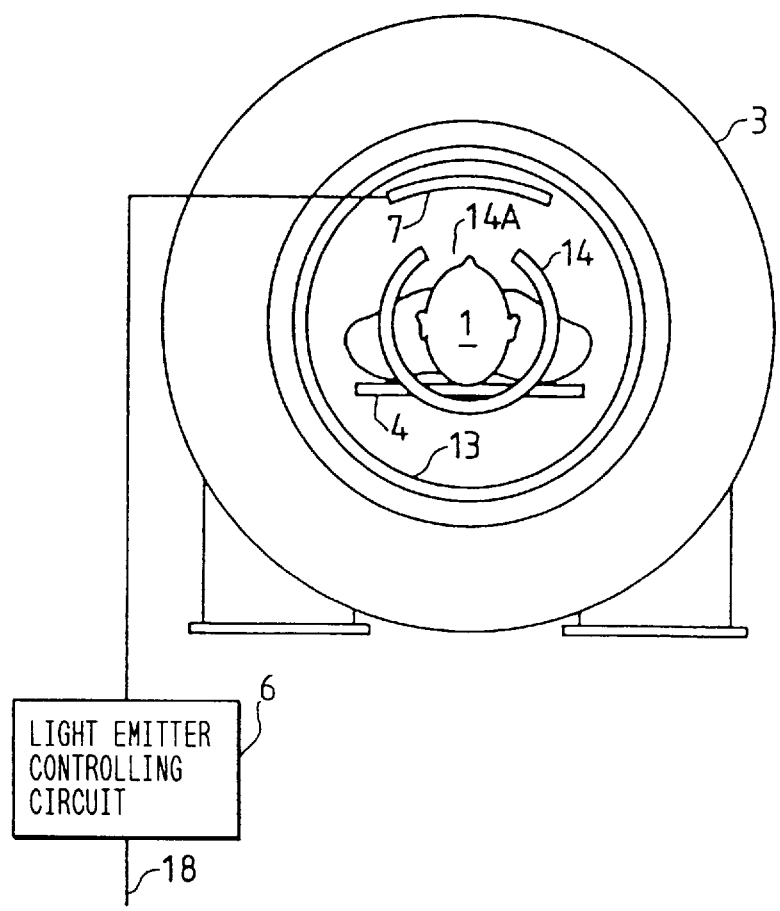
FIG. 4 is a left side view of the superconductive magnet section shown in FIG. 3.

When a Fourier conversion is executed for the NMR signal, which is obtained in this manner two times, an NMR signal (two-dimensional image) corresponding to each coordinate value in the X and Y axial directions is obtained. When this phase encoding is executed also in the z axial direction and the Fourier conversion is executed three times, a three-dimensional image can be constituted, Next, various embodiments of the present invention will be explained. The same numeral in the various drawings indicates the same structure. FIG. 3 is a schematic block diagram of the magnetic resonance inspecting apparatus of a first embodiment of the present invention, in which a method for giving an irritation using a light emitter is employed as an example, when a tomographic image of the head of a person to be inspected 1 is picked up. FIG. 4 is a drawing which is viewed from the end face on the left of the superconductive magnet 3 shown in FIG. 3. In FIG. 3 and FIG. 4, the person to be inspected 1 lies on his back on the tabletop 4 of the patient table 2 and is moved together with the tabletop 4 by a tabletop moving mechanism (not shown in the drawing) so that the head, which is the inspection part, coincides with almost the center of the superconductive magnet 3. The control circuit 5 supplies a control signal for tabletop movement to the patient table 2 so as to move the tabletop 4. The control circuit 5 supplies a control signal 18 to the light emitter control circuit 6. The light emitter control circuit 6 controls a light emitter 7 consisting of a plurality of light emission diodes having a comparatively large light emission area, which will be described later, according to the control signal 18 and emits light with a predetermined color into the magnet space so as to change the quantity of light and the color tone in the magnet space. In the embodiment shown in FIG. 3, the light emitter 7 is installed in the space above the head of the person to be inspected 1. Furthermore, as shown in FIG. 4, a hole 14A is provided in a part of the top of the radio frequency coil 14 in the neighborhood of the head of the person to be inspected 1 so as to prevent blocking of the eyes of the person to be inspected 1.

Figure 5:
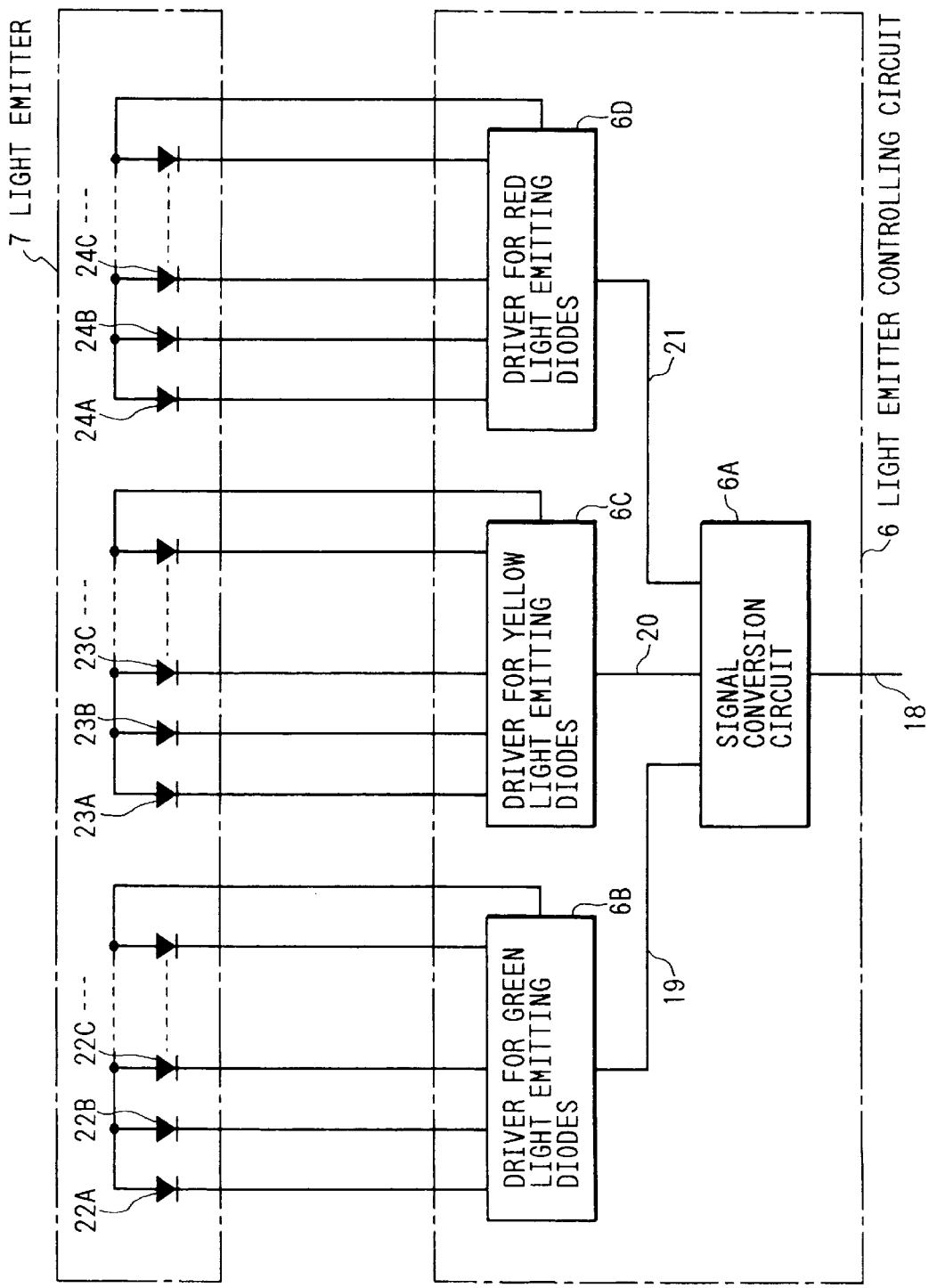
FIG. 5 is a detailed drawing of the section including the light emission control circuit and light emitter shown in FIG. 3.

FIG. 5 is a detailed drawing of the connection relation between the light emitter control circuit 6 and the light emitter 7. In FIG. 5, a signal converter 6A is structured so as to supply a signal 19 to a green light emission diode drive circuit 6B on the basis of a control signal 18 from the control circuit 5, to supply a signal 20 to a yellow light emission diode drive circuit 6C, and to supply a signal 21 to a red light emission diode drive circuit 6D. On the other hand, the light emitter 7 installed inside the magnet has, for example, 10 green plane light emission diodes 22A, 22B, 22C, - - -, 10 yellow plane light emission diodes 23A, 23B, 23C, - - -, and 10 red plane light emission diodes 24A, 24B, 24C, - - -. Each plane light emission diode has a plane light emission area which is comparatively large. The drive circuit 6B controls lighting of the 10 green plane light emission diodes 22A, 22B, 22C, - - - according to the signal 19. The drive circuit 6C controls lighting of the 10 yellow plane light emission diodes 23A, 23B, 23C, - - - according to the signal 20. Furthermore, the drive circuit 6D controls lighting of the 10 red plane light emission diodes 24A, 24B, 24C, - - - according to the signal 21.

When an operator (not shown in the drawing) operates the keys of the console 8, the operation timing and intensity of each of the gradient magnetic field and radio frequency magnetic field are adjusted so as to obtain the best image. Namely, the power sources 9, 10 and 11 for the X, Y and Z gradient magnetic fields and the radio frequency transmission and reception circuit 12 are operated by the control circuit 5, and currents flow through the gradient magnetic field coil 13 and the radio frequency coil 14 including the X, Y and Z coils, and a gradient magnetic field and radio frequency magnetic field are generated in each coil. The NMR signal in the head area of the person to be inspected 1 is detected by the radio frequency coil 14, amplified and detected by the radio frequency transmission and reception circuit 12, and then supplied to the data memory installed in the control circuit 5. The electronic computer 15 executes various processing for a signal in the data memory and calculates and corrects the adjustment data of each magnetic field generation means. By doing this, the operation timing and intensity of each gradient magnetic field and radio frequency magnetic field are adjusted for each person to be inspected.

Figure 6A:
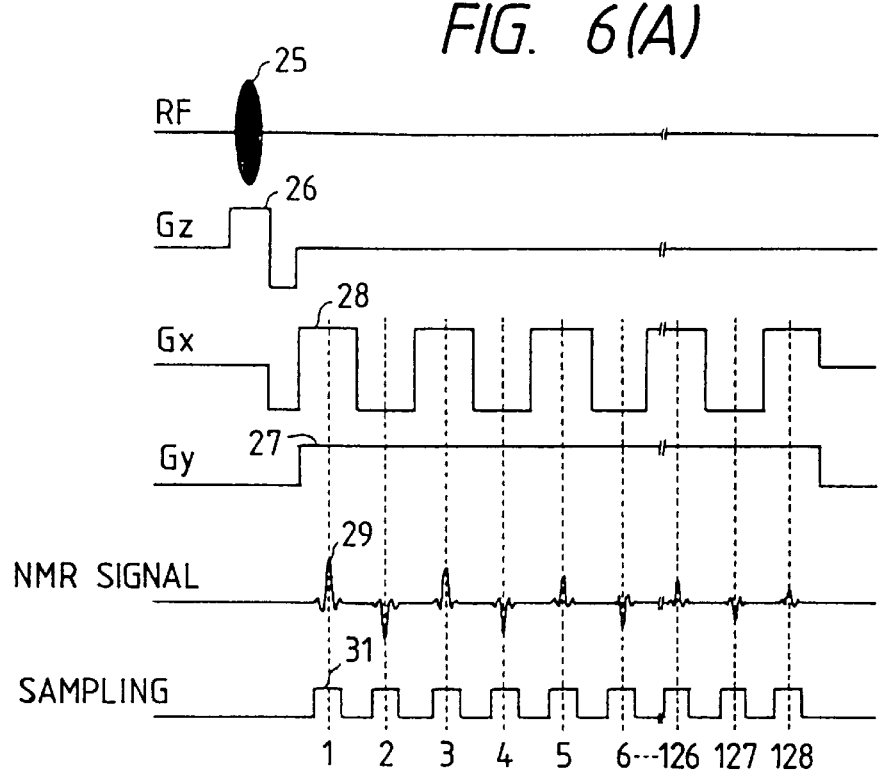
FIG. 6(A) is a pulse diagram which shows a pulse sequence of the echo planer imaging method which is used together with the apparatus shown in FIG. 3.

When the aforementioned adjustment ends, the operator operates the console 8 again and selects the imaging mode which is suited to the inspection object. For example, when the EPI sequence shown in FIG. 6(A) is selected, the pulse 25 of the radio frequency magnetic field RF is generated at the inspection part from the radio frequency transmission and reception circuit 12 by the radio frequency coil 14.

Under the condition that the pulse 26 of the gradient magnetic field Gz for selection of a 10 mT/m slice is applied, the amplitude is modulated by the Gaussian waveform so as to have a frequency band of about 2 KHz so as to excite a nuclear spin with a slice thickness of 5 mm. The excited nuclear spin attenuates at a relaxation time of T2. Numeral 28 indicates a pulse of the gradient magnetic field Gx for frequency encoding and 27 indicates a pulse of the gradient magnetic field Gy for phase encoding and they are applied in the X direction, and Y direction respectively. The pulse 28 is switched to positive or negative alternately at a time interval of τ, 3τ, 5τ, - - - immediately after the pulse 25 of the radio frequency magnetic field. The pulse 27 is applied at a fixed value during the whole observation time. At a point of time of 2 tau, 4 tau, - - - when the integral amount the pulse 28 is zero, the NMR signal 29 is detected as an echo signal. Detections are recorded as discrete digital data of 256 points. When the NMR signal 29 is repeated 128 times, a phase corresponding to the integral amount of the pulse 27 of the gradient magnetic field corresponding to the coordinate in the Y axial direction is reflected to the NMR signal. When 256 by 128 matrix data is subjected to two-dimensional Fourier conversion by the electronic computer 15, an image at the inspection part is reconfigured. The reconfigured image signal is sent to the monitor 16 or the camera 17, displayed on a CRT or film, and is used for diagnosis.

Figure 6B:
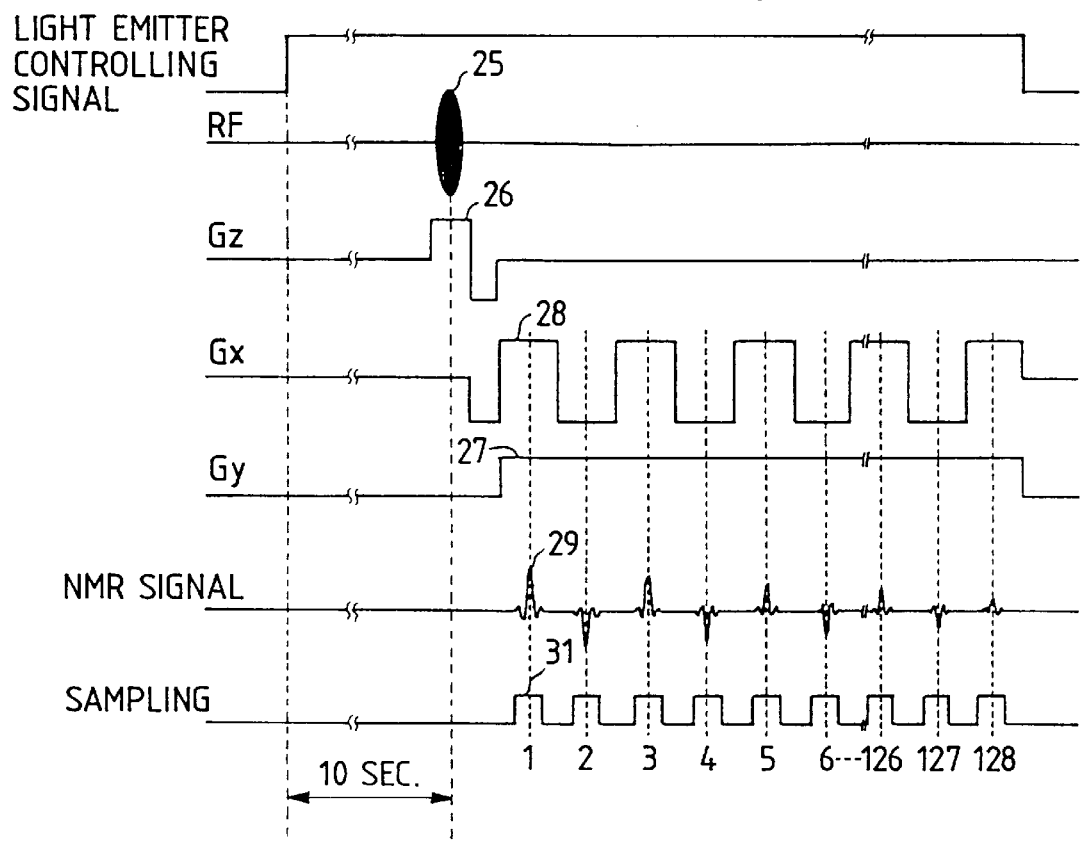
FIG. 6(B) is a pulse diagram which shows a pulse sequence of the echo planer imaging method which is used together with the apparatus shown in FIG. 3 and is related to a light emitter controlling signal.

Next, when the object of the inspection is to measure the activation status (to obtain function information of the visual central nerve) of the brain tissue of a person to be inspected quantitatively, the operator operates the console 8 again so as to select the imaging mode for turning the light emitter 7 in the magnet on. As an example, for making the time accuracy of the function of the visual central nerve exact, measurement starts 10 seconds after the light emitter lights (see FIG. 6(B)). Except for the light emitter control signal, the NMR signal is measured according to the timing of the sequence shown in FIG. 6(A) so as to reconfigure an image and the image is stored in the image memory of the computer 15. To compare and inspect an image which is picked up by the sequence shown in FIG. 6(A) and an image which is picked up by the sequence shown in FIG. 6(B), the two images are displayed on the same CRT (or film) side by side at the same time. Furthermore, to make the variation clear, the difference between the two images is calculated and then the images are displayed.

According to this embodiment, a plurality of light emission diodes are employed and the light quantity, color spectra, characters, and pictures can be given to a person to be inspected as information, so that diagnostic images of a high level perceptive function can be obtained. Furthermore, the time for activating the brain tissue can be selected before or during measurement of the NMR signal so as to be synchronized with the imaging accurately.

In this embodiment, a plurality of light emission diodes incorporated on a plane are used as light emitters. However, a lamp, electro-luminescent element, and liquid crystal, which are arranged inside and outside the magnet, may be used so as to give various irritations, so that the same effect can be obtained.

Figure 7:
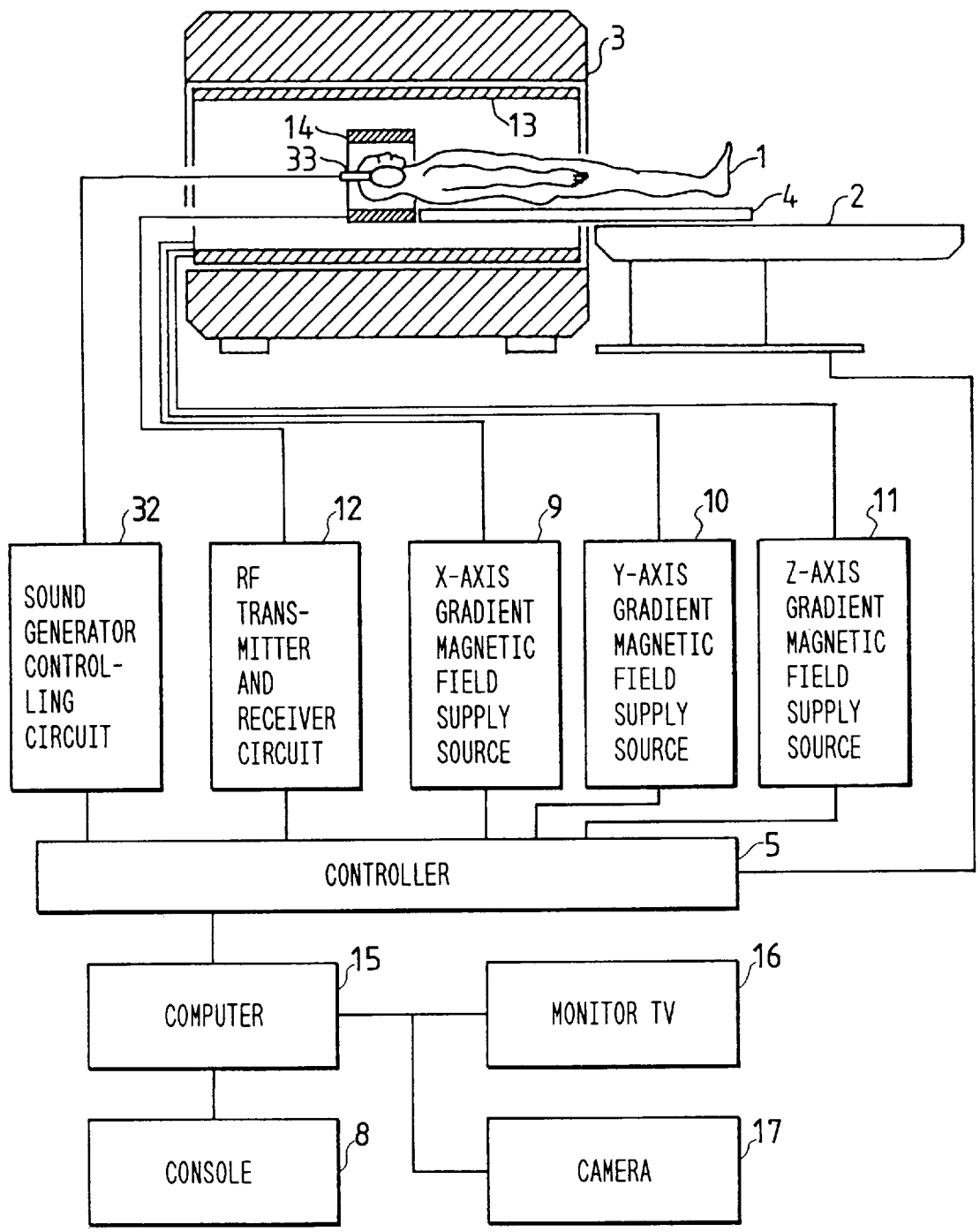
FIG. 7 is a block diagram of a second embodiment of the magnetic resonance inspecting apparatus based on the present invention.

FIG. 7 is a schematic block diagram of the magnetic resonance inspecting apparatus of a second embodiment of the present invention, in which a method for giving an irritation by a sounding body is used as an example when a tomographic image of the head of the person to be inspected 1 is picked up. The person to be inspected 1 lies on his back on the tabletop 4 of the patient table 2 and is moved together with the tabletop 4 by a tabletop moving mechanism (not shown in the drawing) so that the head which is the inspection part coincides with almost the center of the superconductive magnet 3. The control circuit 5 supplies a control signal for tabletop movement to the patient table 2 so as to move the tabletop 4. The control circuit 5 supplies a control signal 18 to the sound generator controlling circuit 32. The sound generator controlling circuit 32 controls sound generators 33 such as headphones attached to the ears of the person to be inspected 1 by a structure for blocking an external sound, which will be described later, according to the control signal 18 and gives information of various sounds to the person to be inspected 1.

The operator operates the console 8 in the same way as with the first embodiment so as to promote the target inspection. A difference from the first embodiment is that the measurement is not of the function status of the visual central nerve, but relates to measurement of the function status of the auditory central nerve.

Figure 8:
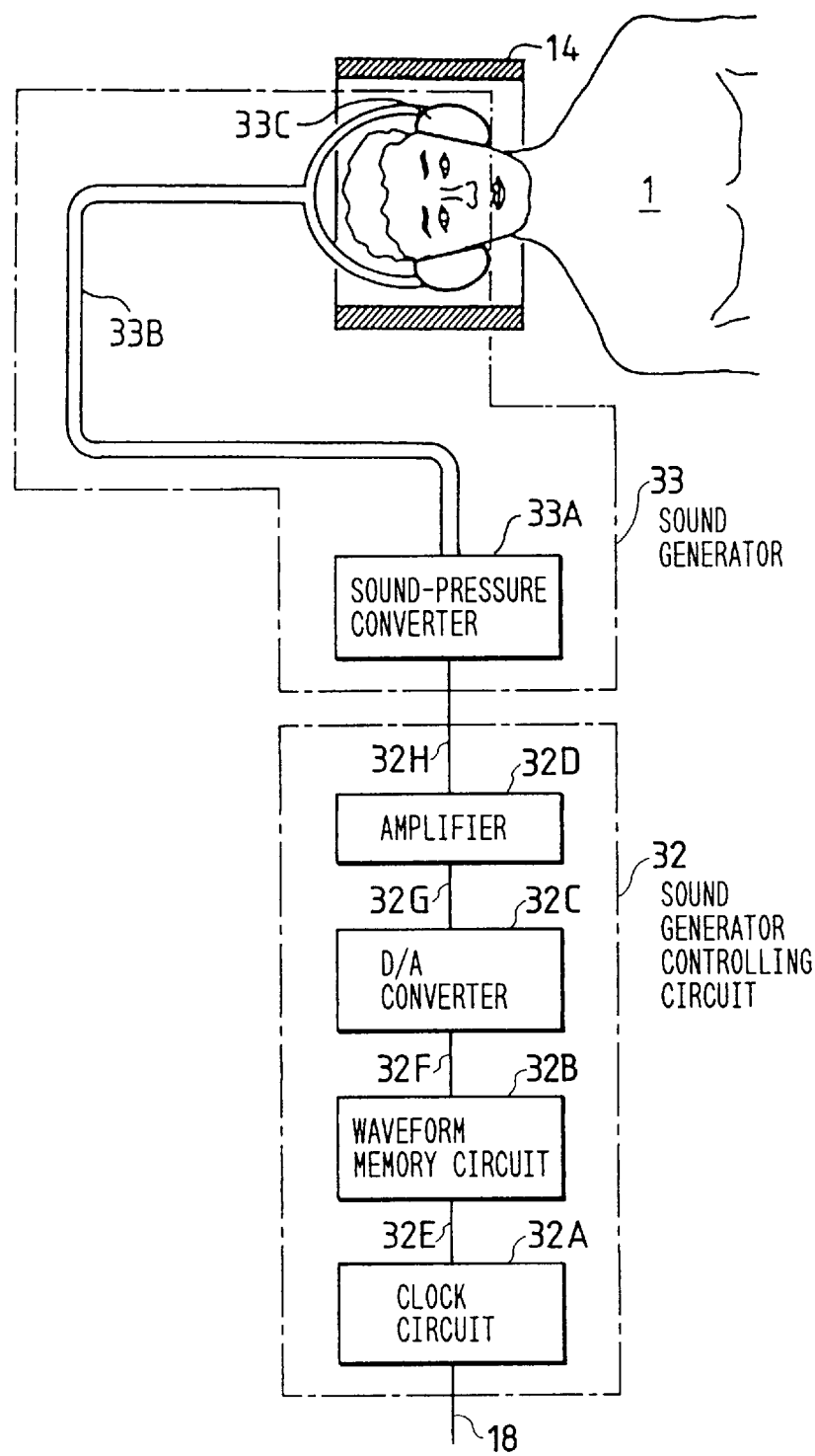
FIG. 8 is a detailed drawing of the section including the sounding body control circuit and sound emitter shown in FIG. 7.

FIG. 8 is a detailed drawing of the sound generator controlling circuit 32 and the sound generators 33 attached to the person to be inspected. A control signal from the control circuit 5 is inputted to a clock circuit 32A. The clock circuit 32A generates a scanning signal 32E from the address of a waveform memory circuit 32B where various waveforms are recorded according to the control signal. An output signal 32F of the waveform memory circuit 32B is transmitted to a D-A conversion circuit 32C. A waveform signal 32G, which is converted to a voltage by the D-A conversion circuit 32C, is switched to an electric signal 32H, which is amplified to the desired amplitude by an amplifier 32D and applied to a sound pressure conversion circuit 33A. The sound pressure conversion circuit 33A has a speaker which is, for example, incorporated in a sealed container so as to convert an electric signal to an air pressure. This air pressure is supplied to sound generators 33C close to the ears of the person to be inspected 1 in the superconductive magnet by a pressure supply pipe 33B. The headphones 33C and the pressure supply pipe 33B are made of materials which will not affect the characteristics of the other means for detecting the NMR signal, that is, the static magnetic field, gradient magnetic field, and radio frequency magnetic field. Furthermore, they are configured so as not to transmit an external sound to the person to be inspected 1.

According to this embodiment, function diagnostic information of the auditory cortex by sound can be obtained. Furthermore, an effect can be obtained such that an uncomfortable noise (a vibration noise of the gradient magnetic field coil) accompanying inspection is blocked and no unpleasant feeling is given to the person to be inspected.

Figure 9:
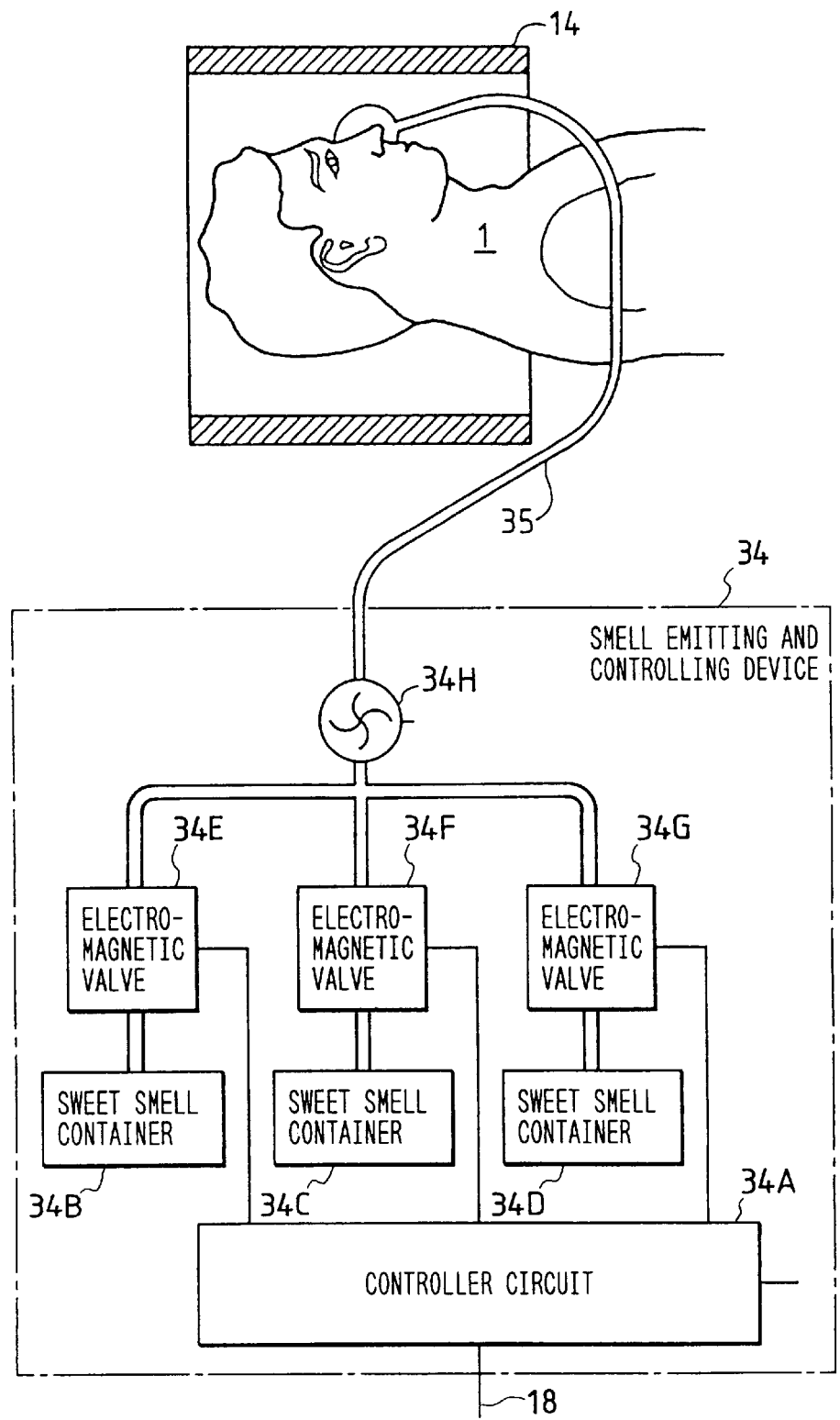
FIG. 9 is a detailed drawing of the section including the smell emitter controller of a third embodiment of the magnetic resonance inspecting apparatus based on the present invention.

FIG. 9 is a block diagram of a smell emitter controller used for the magnetic resonance inspecting apparatus of a third embodiment of the present invention, in which a method for giving an irritation by a smell emitter is employed as an example, when a tomographic image of the head of the person to be inspected 1 is picked up. In the same way as with the second embodiment, the person to be inspected 1 lies on his back on the tabletop 4 of the patient table 2 and is moved together with the tabletop 4 by a tabletop moving mechanism (not shown in the drawing) so that the head which is the inspection part coincides with almost the center of the superconductive magnet 3. The control circuit 5 supplies a control signal for tabletop movement to the patient table 2 so as to move the tabletop 4. The control circuit 5 supplies a control signal 18 to the smell emitter controller 34. The smell emitter controller 34 including various smell elements, which will be described later, gives information of various smells to the person to be inspected 1 via a pipe 35 attached to the nose of the person to be inspected 1 according to the control signal 18.

Containers 34B, 34C and 34D containing three types of smell elements are arranged in the smell emitter controller 34 and solenoid valves 34E, 34F and 34G are attached to them, respectively. The outlet of each solenoid valve is connected to an air blower 34H and the outlet of the air blower 34H is connected to the pipe 35 attached to the nose of the person to be inspected 1. A control circuit 34A controls the operations of the solenoid valves and air blower according to the control signal 18.

The operator operates the console 8 in the same way as with the second embodiment so as to promote the target inspection. A difference from the second embodiment is that the measurement is not of the function status of the auditory central nerve, but relates to measurement of the function status of the smell central nerve.

According to this embodiment, function diagnostic information of the smell central nerve by smell can be obtained. Furthermore, when laughing gas is added to the smell emitter controller 34, it can be used for inspection in the anesthetized and rest condition.

Figure 10:
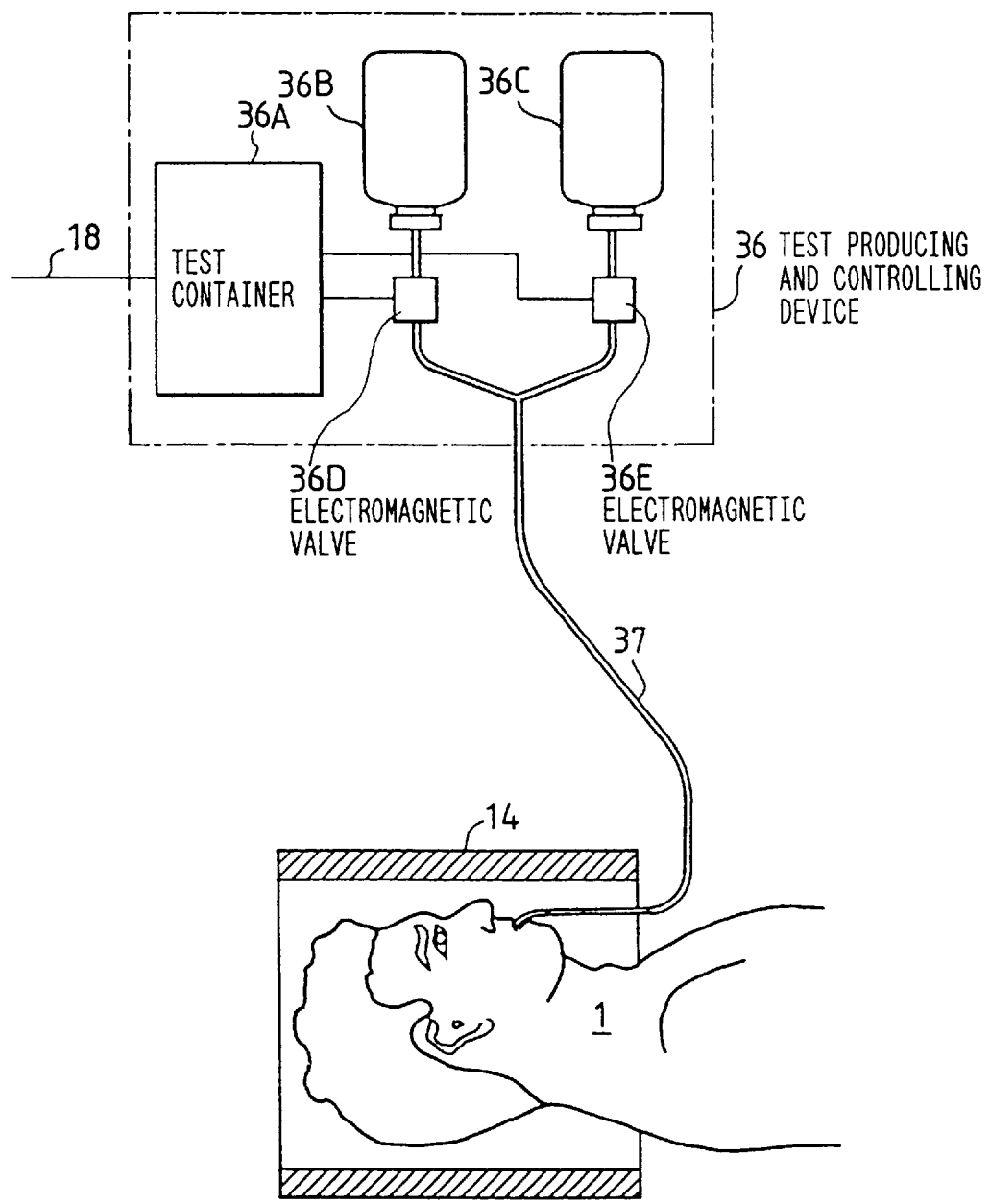
FIG. 10 is a detailed drawing of the section including a taste producer controller of a fourth embodiment of the magnetic resonance inspecting apparatus based on the present invention.

FIG. 10 is a block diagram of a taste producer controller used for the magnetic resonance inspecting apparatus of the fourth embodiment of a present invention, in which a method for giving an irritation by taste is employed as an example, when a tomographic image of the head of the person to be inspected 1 is picked up. In the same way as with the second embodiment, the person to be inspected 1 lies on his back on the tabletop 4 of the patient table 2 and is moved together with the tabletop 4 by a tabletop moving mechanism (not shown in the drawing) so that the head which is the inspection part coincides with almost the center of the superconductive magnet 3. The control circuit 5 supplies a control signal for tabletop movement to the patient table 2 so as to move the tabletop 4. The control circuit 5 supplies a control signal 18 to the taste producer controller 36. The taste producer controller 36, including various taste elements which will be described later, gives information of various tastes to the person to be inspected 1 via a pipe 37 attached to the mouth of the person to be inspected 1 according to the control signal 18.

Containers 36B and 36C containing two types of taste elements are arranged in the taste producer controller 36 and solenoid valves 36D and 36E are attached to them, respectively. The outlet of each solenoid valve is connected to the pipe 37 attached to the mouth of the person to be inspected 1. A control circuit 36A controls the operations of the solenoid valves according to the control signal 18.

The operator operates the console 8 in the same way as with the second embodiment so as to promote the target inspection. A difference from the second embodiment is that the measurement is not of the function status of the auditory central nerve, but relates to measurement of the function status of the gustatory central nerve.

According to this embodiment, function diagnostic information of the gustatory central nerve by taste can be obtained.

Figure 11:
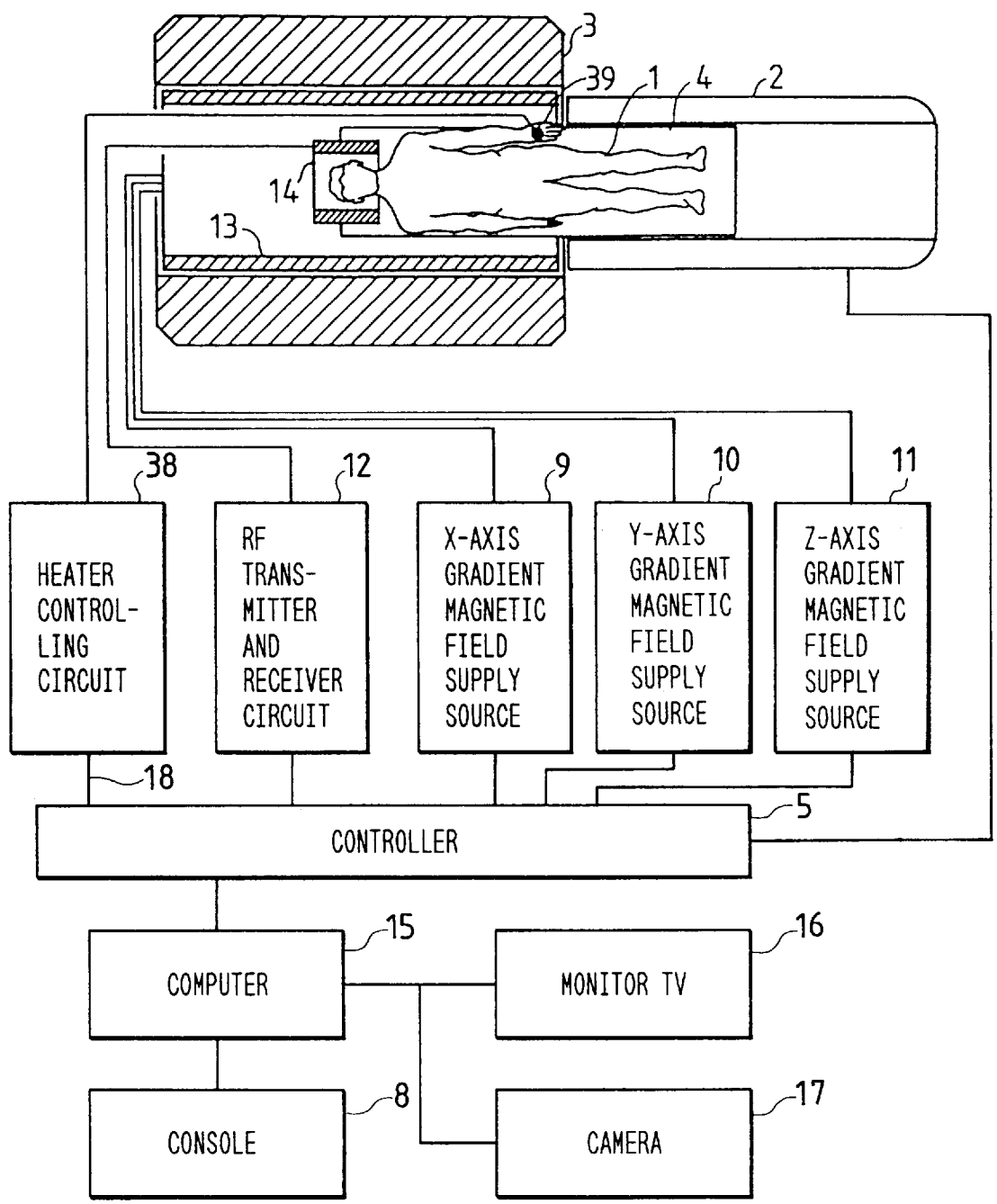
FIG. 11 is a block diagram of a fifth embodiment of the magnetic resonance inspecting apparatus based on the present invention.

FIG. 11 is a schematic block diagram of the magnetic resonance inspecting apparatus of a fifth embodiment of the present invention to, in which a method for giving an irritation using a heating unit is applied. The diagram shows an example in which a tomographic image of the head of the person to be inspected 1 is picked up. The person to be inspected 1 lies on his back on the tabletop 4 of the patient table 2. The person is moved together with the tabletop 4 by a tabletop moving mechanism (not shown in the drawing) so that the head which is the inspection part coincides with almost the center of the superconductive magnet 3. The control circuit 5 supplies a control signal for tabletop movement to the patient table 2 so as to move the tabletop 4. The control circuit 5 supplies a control signal 18 to the heating unit control circuit 38. The heating unit control circuit 38 controls a heating unit 39 attached to the palm of the hand of the person to be inspected 1 and gives information of heat to the person to be inspected 1 according to the control signal 18.

The operator operates the console 8 in the same way as with the first embodiment so as to promote the target inspection. A difference from the first embodiment is that the measurement is not of the function status of the visual central nerve, but relates to measurement of the function status of the heat sensitive central nerve.

Figure 12:
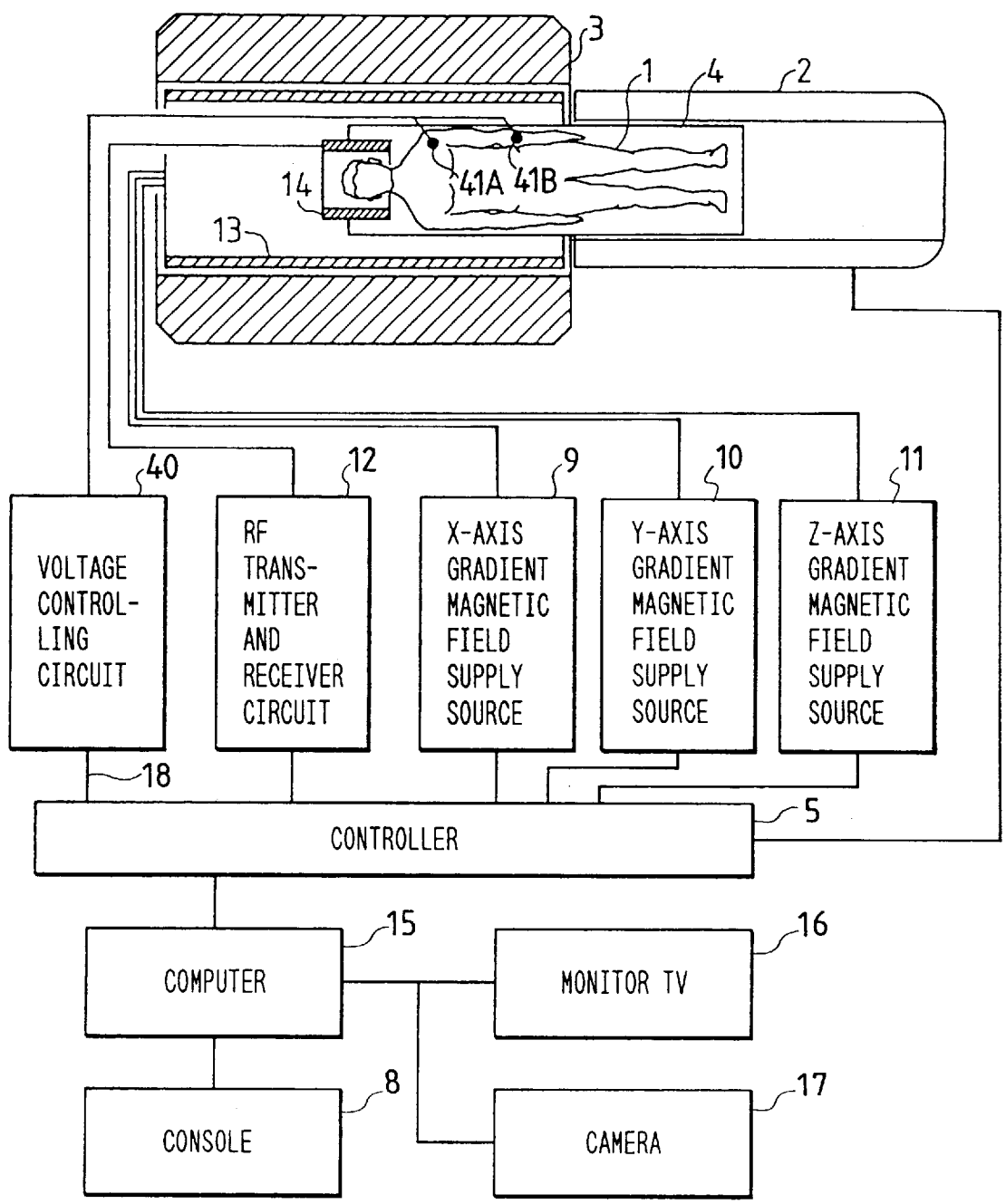
FIG. 12 is a block diagram of a sixth embodiment of the magnetic resonance inspecting apparatus based on the present invention.

FIG. 12 is a schematic block diagram of the magnetic resonance inspecting apparatus of a sixth embodiment of the present invention, in which a method for giving an irritation using electricity is applied employed. The diagram shows an example in which a tomographic image of the head of the person to be inspected 1 is picked up. The person to be inspected 1 lies on his back on the tabletop 4 of the patient table 2. The person is moved together with the tabletop 4 by a tabletop moving mechanism (not shown in the drawing) so that the head which is the inspection part coincides with almost the center of the superconductive magnet 3. The control circuit 5 supplies a control signal for tabletop movement to the patient table 2 so as to move the tabletop 4. The control circuit 5 supplies a control signal 18 to a voltage control circuit 40. The voltage control circuit 40 applies a voltage to electrodes 41A and 41B attached to an arm of the person to be inspected 1 so as to give an electric irritation to the person to be inspected 1 according to the control signal 18.

The operator operates the console 8 in the same way as with the first embodiment so as to promote the target inspection. A difference from the first embodiment is that the measurement of the function status of the visual central nerve, but relates measurement of the function status of the electric shock central nerve.

According to this embodiment, by asking the person to be inspected 1 to exercise his arms in response to the signal of a light electric irritation before starting of the inspection, function diagnostic information of motion cortex can be obtained.

According to the present invention, an irritation can be given to the tissue of the human body from the outside and the NMR signal is detected in accurate synchronization with the timing for giving the irritation. Therefore, a magnetic resonance inspecting method and an apparatus which will provide a clear understanding of the relation between irritation and tissue action can be obtained.

What is claimed is:

1. A magnetic resonance inspecting method using nuclear magnetic resonance comprising the steps of generating a static magnetic field in a predetermined space including an inspection object, generating each of a gradient magnetic field and a radio frequency magnetic field in said space with a predetermined timing and intensity, detecting a nuclear magnetic resonance signal from said inspection object, and processing said detected signal, wherein said method includes the further step of applying an irritation to a sense organ of said inspection object substantially in synchronism with a predetermined timing for generating each of said gradient magnetic field and said radio frequency magnetic field, wherein the detecting of the nuclear magnetic resonance signal from said inspection object is carried out immediately after the applying of said irritation.

2. The magnetic resonance inspecting method according to claim 1, wherein said irritation is effected by applying light to said inspection object.

3. The magnetic resonance inspecting method according to claim 1, wherein said irritation is effected by applying sound to said inspection object.

4. The magnetic resonance inspecting method according to claim 1, wherein said irritation is effected by supplying a substance which has a predetermined smell to said inspection object.

5. The magnetic resonance inspecting method according to claim 1, wherein said irritation is effected by supplying a substance which has a predetermined taste to said inspection object.

6. The magnetic resonance inspecting method according to claim 1, wherein said irritation is effected by applying an electrical impulse to said inspection object.

7. The magnetic resonance inspecting method according to claim 1, wherein said irritation is effected by applying heat to said inspection object.

8. A magnetic resonance inspecting method according to claim 1, further comprising the step of displaying first and second data, said detecting step including the steps of detecting the nuclear magnetic resonance signal when said irritation is applied and detecting the nuclear magnetic resonance signal when said irritation is not applied, and said processing step including the steps of processing the nuclear magnetic resonance signal detected when said irritation is applied so as to produce said first data and processing the nuclear magnetic resonance signal detected when said irritation is not applied so as to produce said second data.

9. A magnetic resonance inspecting method according to claim 8, wherein said displaying step includes the steps of displaying a difference between said first and second data.

10. A magnetic resonance inspecting apparatus comprising:
    magnetic field generating means for generating a static magnetic field, a gradient magnetic field and a radio frequency magnetic field in a predetermined space including an inspection object;
    means for applying an irritation to a sense organ of said inspection object substantially in synchronism with a predetermined timing for generating each of said gradient magnetic field and radio frequency magnetic field;
    signal detection means, installed in said predetermined space, for detecting a nuclear magnetic resonance signal from the inspection object;
    an electronic computer, responsive to said detected nuclear magnetic resonance signal, for performing a predetermined operation on said nuclear magnetic resonance signal, and for outputting an operation result; and
    display means for displaying said operation result outputted by said electronic computer.

11. A magnetic resonance inspecting apparatus according to claim 10 wherein said irritation applying means is of a physical irritation applying type, and further including means for physically shielding a part of said inspection object so as to prevent irritation other than the physical irritation by said irritation applying means from substantially affecting the corresponding sense organ of said inspection object.

12. The magnetic resonance inspecting apparatus according to claim 10, wherein said irritation applying means includes a light source for emitting light at a selected wavelength at said inspection object.

13. The magnetic resonance inspecting apparatus according to claim 10, wherein irritation applying means includes a device for supplying sound to said inspection object.

14. The magnetic resonance inspecting apparatus according to claim 13, wherein said device for supplying sound includes an element for converting an electrical signal to an air pressure, at least one conduit for carrying the air pressure, and a sound generator coupled to said conduit and responsive to said air pressure for generating sound in the vicinity of said inspection object.

15. The magnetic resonance inspecting apparatus according to claim 10, wherein said means for applying an irritation includes a device for supplying a selected substance which has a predetermined smell to said inspection object.

16. The magnetic resonance inspecting apparatus according to claim 10, wherein irritation applying means includes a device for supplying a selected substance having a predetermined taste to said inspection object.

17. The magnetic resonance inspecting apparatus according to claim 10, wherein irritation applying means includes a device for applying an electrical charge to said inspection object.

18. The magnetic resonance inspecting apparatus according to claim 10, wherein irritation applying means includes a device for applying heat to said inspection object.

19. A magnetic resonance inspecting apparatus comprising:
    magnetic field generating means for generating a static magnetic field, a gradient magnetic field, and a radio frequency magnetic field in a predetermined space including an inspection object;
    means for activating brain tissue of said inspection object;
    signal detection means, installed in said predetermined space, for detecting a nuclear magnetic resonance signal from the inspection object;
    an electronic computer, responsive to said detected nuclear magnetic resonance signal, for performing a predetermined operation on said nuclear magnetic resonance signal , and for outputting an operation result; and
    control means, which is connected between said electronic computer and both of said magnetic field generation means and said brain tissue activation means , for effecting control so that said activation of the brain tissue is executed substantially in synchronism with a predetermined timing for generating each of said gradient magnetic field and radio frequency magnetic field; and
    display means for displaying said operation result outputted by said electronic computer.

20. A method of inspecting an active function of a brain of a living body using a magnetic resonance phenomenon, comprising the steps of:
    (1) arranging a head portion of the living body in a static magnetic field, and applying a gradient magnetic field and a radio frequency magnetic field according to a predetermined pulse sequence to effect acquisition of first image data of the brain including a portion to be inspected;
    (2) externally applying to a sense organ of the living body an irritation to which the portion to be inspected in the brain reacts during a period of time after effecting the acquisition of the first image data;

(3) restarting the predetermined pulse sequence of applying the gradient magnetic field and the radio frequency magnetic field after lapse of a period of time from the start of the applying of the irritation to the sense organ to effect acquisition of second image data of the portion to be inspected activated by the irritation; and (4) calculating a difference between the first and second image data to effect acquisition of third image data in which a relation between the applied irritation and tissue active information at the portion to be inspected reacted to the irritation is indicated.

21. A method of inspecting an active function of a brain of a living body according to claim 20, further comprising the steps of forming a first image on the basis of the first image data and forming a second image on the basis of the second image data, displaying the first and second images adjacent to each other so as to enable contrasting of the first and second images with each other.

22. A method of inspecting an active function of a brain of a living body according to claim 20, further comprising the step of shielding the sense organ of the living body from an irritation other than the applied irritation to the sense organ so as to prevent any other irritation from being applied thereto.

23. A method of inspecting an active function of a brain of a living body according to claim 20, wherein the irritation which is externally applied is produced until the acquisition of the second image data is completed.

24. A method of inspecting an active function of a brain of a living body according to claim 20, wherein an amount of the externally applied irritation to the sense organ is variably settable.

25. A method of inspecting an active function of a brain of a living body according to claim 20, wherein the lapse of the period of time after application of the irritation until the predetermined pulse sequence is restarted is selectable.

26. A method of inspecting an active function of a brain of a living body according to claim 20, wherein the step of externally applying irritation includes directly applying the irritation to the sense organ.

27. An inspecting apparatus of an active function of a brain of a living body using a magnetic resonance phenomenon, comprising:

(1) means for arranging a head portion of the living body in a static magnetic field, and for applying a gradient magnetic field and a radio frequency magnetic field according to a predetermined pulse sequence to effect acquisition of first image data of the brain including a portion to be inspected;

(2) means for externally applying to a sense organ of the living body an irritation to which the portion to be inspected in the brain reacts during a period of time after effecting the acquisition of the first image data;

(3) means for restarting the predetermined pulse sequence of applying the gradient magnetic field and the radio frequency magnetic field after lapse of a period of time from the start of the applying of the irritation to the sense organ to effect acquisition of second image data of the portion to be inspected activated by the irritation; and (4) means for calculating a difference between the first and second image data to effect acquisition of third image data in which a relation between the applied irritation and tissue active information at the portion to be inspected reacted to the irritation is indicated.

28. An inspecting apparatus of an active function of a brain of a living body according to claim 27, further comprising means for forming a first image on the basis of the first image data and for forming a second image on the basis of the second image data, means for displaying the first and second images adjacent to each other so as to enable contrasting of the first and second images with each other.

29. An inspecting apparatus of an active function of a brain of a living body according to claim 27, further comprising a shield disposed with respect to the living body for shielding the sense organ of the living body from an irritation other than the applied irritation to the sense organ so as to prevent any other irritation from being applied thereto.

30. An inspecting apparatus of an active function of a brain of a living body according to claim 27, wherein the means for externally applying the irritation applies the irritation until the acquisition of the second image data is completed.

31. An inspecting apparatus of an active function of a brain of a living body according to claim 27, wherein the means for externally applying the irritation applies a variably settable amount of the externally applied irritation to the sense organ.

32. An inspecting apparatus of an active function of a brain of a living body according to claim 27, wherein the means for restarting the predetermined pulse sequence effects restarting after lapse of a settable period of time after the application of the irritation.

33. An inspecting apparatus of an active function of a brain of a living body according to claim 27, wherein the means for externally applying irritation directly applies irritation to the sense organ.

* * * * *